(12) United States Patent
Littau et al.

(10) Patent No.: US 7,119,893 B2
(45) Date of Patent: Oct. 10, 2006

(54) DETERMINATION OF CENTER OF FOCUS BY PARAMETER VARIABILITY ANALYSIS

(75) Inventors: Michael E. Littau, Bend, OR (US); Christopher J. Raymond, Bend, OR (US)

(73) Assignee: Accent Optical Technologies, Inc., Bend, OR (US)

( * ) Notice: Subject to any disclaimer, the term of this patent is extended or adjusted under 35 U.S.C. 154(b) by 0 days.

(21) Appl. No.: 10/820,911

(22) Filed: Apr. 8, 2004

(65) Prior Publication Data

US 2004/0233445 A1 Nov. 25, 2004

Related U.S. Application Data

(60) Provisional application No. 60/462,353, filed on Apr. 10, 2003.

(51) Int. Cl.
*G01B 9/00* (2006.01)
*G01B 11/00* (2006.01)
*G01B 11/14* (2006.01)

(52) U.S. Cl. .................. 356/124; 356/401; 356/625

(58) Field of Classification Search ........ 356/124–127, 356/627, 628, 630, 635, 636, 399–401; 430/22, 430/30; 355/53, 55; 250/548
See application file for complete search history.

(56) References Cited

U.S. PATENT DOCUMENTS

| 4,710,642 A | 12/1987 | McNeil |
| 4,759,626 A | 7/1988 | Kroko |
| 4,863,548 A | 9/1989 | Lee |

| 2002/0038196 A1 | 3/2002 | Johnson et al. |
| 2002/0131055 A1 | 9/2002 | Niu et al. |
| 2002/0135783 A1 | 9/2002 | Opsal et al. |

(Continued)

FOREIGN PATENT DOCUMENTS

WO WO-WO 01/97279 A2 12/2001

(Continued)

OTHER PUBLICATIONS

Ausschnitt, Christopher P., et al., "Seeing the forest for the trees: a new approach to CD control", *Proc. SPIE vol. 3332*, (1998),212-220.

(Continued)

*Primary Examiner*—Gregory J. Toatley, Jr.
*Assistant Examiner*—Gordon J. Stock, Jr.
(74) *Attorney, Agent, or Firm*—Stephen A. Slusher; Philip D. Askenazy; Peacock Myers, P.C.

(57) ABSTRACT

Methods for the determination of center of focus and process control for a lithographic tool. Diffraction signatures are obtained from a plurality of diffraction structures located within multiple different focus setting fields. Variability of diffraction signatures with each field are determined, by direct analysis or comparison to a library. The variation or uniformity may be represented by any measure, including the standard deviation or the range of values of a chosen feature of a library of theoretical diffraction structures or the variability or uniformity of the diffraction signatures themselves, such as by RMS difference or intensity range. The methods may be used for process control and monitoring of focus drift by determining intra-field variation of diffraction signatures of multiple diffraction structures in a series of wafers.

34 Claims, 7 Drawing Sheets

Focus = -0.1 μm

Focus = 0.0 μm

Focus = +0.1 μm

Signature Range vs Focus position (μm)

U.S. PATENT DOCUMENTS

| | | | |
|---|---|---|---|
| 4,920,273 A | 4/1990 | Sacks et al. | |
| 5,044,750 A | 9/1991 | Shamble | |
| 5,164,790 A | 11/1992 | McNeil et al. | |
| 5,241,369 A | 8/1993 | McNeil et al. | |
| 5,266,790 A | 11/1993 | Markle et al. | |
| 5,703,692 A | 12/1997 | McNeil et al. | |
| 5,712,707 A | 1/1998 | Ausschnitt et al. | |
| 5,867,276 A | 2/1999 | McNeil et al. | |
| 5,877,860 A | 3/1999 | Borden | |
| 5,889,593 A | 3/1999 | Bareket | |
| 5,912,741 A | 6/1999 | Carter et al. | |
| 5,952,132 A | 9/1999 | King et al. | |
| 5,953,128 A | 9/1999 | Ausschnitt et al. | |
| 6,005,669 A | 12/1999 | Pahk et al. | |
| 6,088,113 A | 7/2000 | Kim | |
| 6,100,985 A | 8/2000 | Scheiner et al. | |
| 6,429,930 B1 * | 8/2002 | Littau et al. | 356/124 |
| 6,501,534 B1 * | 12/2002 | Singh et al. | 355/55 |
| 6,606,152 B1 | 8/2003 | Littau et al. | |
| 6,728,663 B1 | 4/2004 | Krukar et al. | |

FOREIGN PATENT DOCUMENTS

| | | |
|---|---|---|
| WO | WO-WO 03/032085 | 4/2003 |

OTHER PUBLICATIONS

Bao, Junwei, et al., "A Focus Tests based on Scatterometry", *Slide Presentation*, http://bcam.berkeley.edu/archive/ilp98/junwei/1.html, Berkeley, Computer Aided Manufacturing, University of California at Berkeley, Berkeley, CA., (Mar. 1998).

Edwards, Rick, et al., "Characterization of Autofocus Uniformity and Precision on ASML Steppers using the Phase Shift Focus Monitor Reticle", *Proc. SPIE Vo. 3051*, (1997),448-455.

Niu, X., et al., "In-Situ Sensing by Specular Spetroscopic Scatterometry", *Slide Presentation*, http://www.bcam.eecs.berkeley.edu/archive/ilp98/junwei/1.html, Berkeley Computer Aided Manufacturing, University of California at Berkeley, Berkeley, CA.,(Mar. 1998).

Niu, Xinhui, et al., "Specular Spectroscopic Scatterometry in DUV Lithography", *Proc. SPIE Metrology, Inspection, and Process Control for Microlithography XIII*, vol. 3677, SPIE, Santa Clara, California,(Mar. 1999), 159-168.

Raymond, Christopher J., et al., "Angle-resolved scatterometry for semiconductor manufacturing", *Microlithography World*, (Winter 2000), 18-23.

* cited by examiner

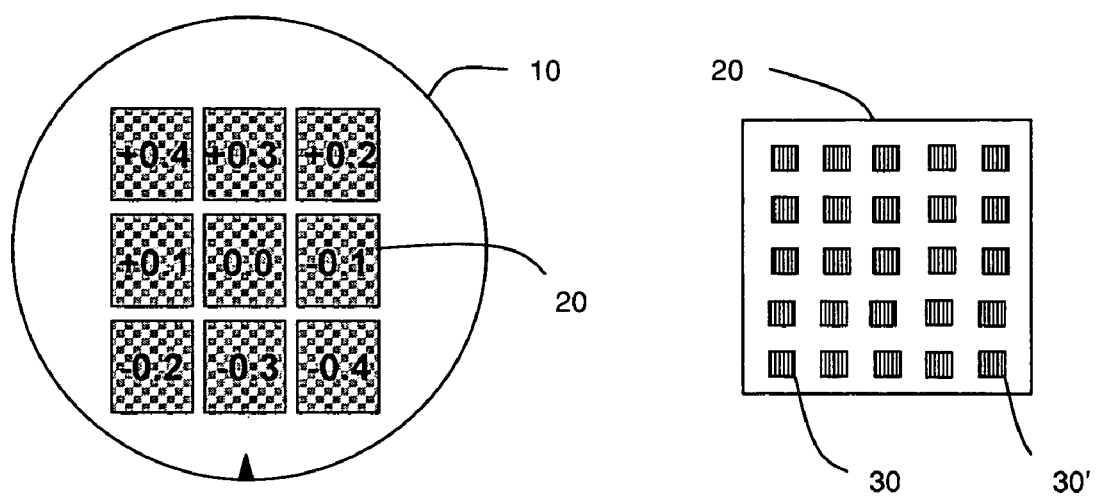
FIGURE 1A
FIGURE 1B
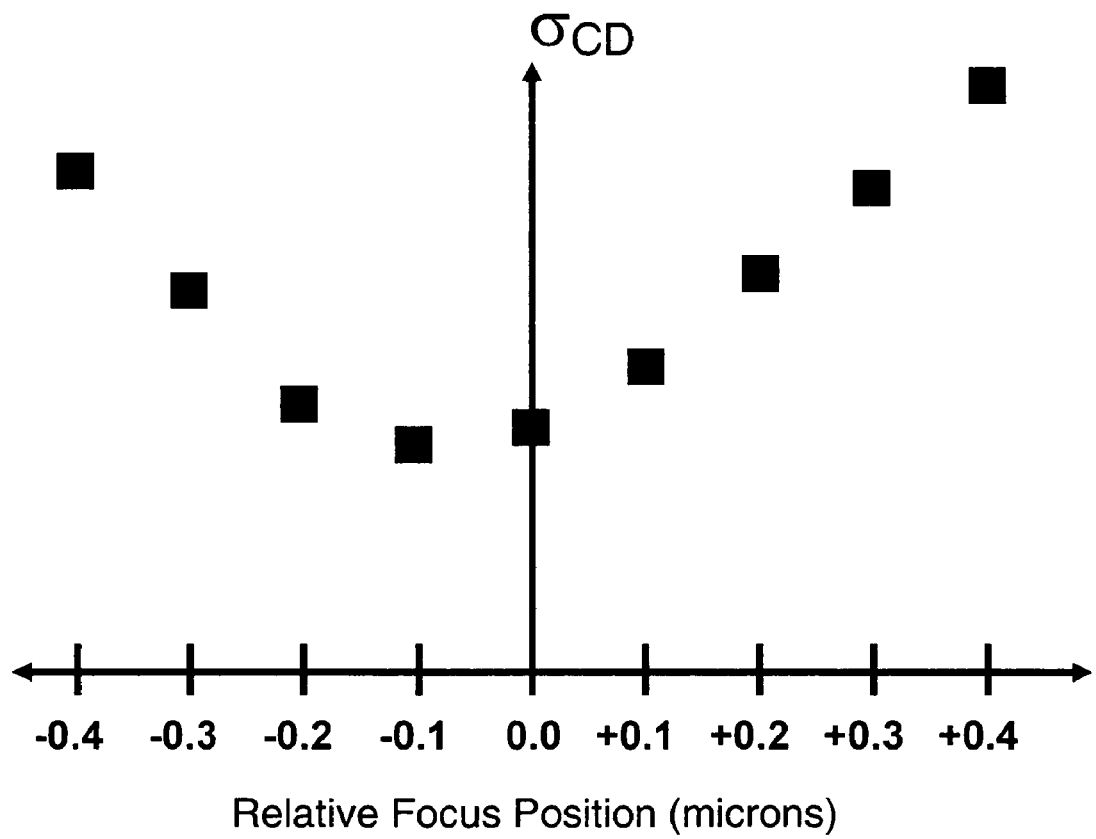
FIGURE 2

DETERMINATION OF CENTER OF FOCUS BY PARAMETER VARIABILITY ANALYSIS

CROSS-REFERENCE TO RELATED APPLICATION

This application claims the benefit of the filing of U.S. Provisional Patent Application Ser. No. 60/462,353, entitled Determination Of Center Of Focus In Lithographic Applications, filed on Apr. 10, 2003, the specification of which is incorporated herein by reference.

BACKGROUND OF THE INVENTION

1. Field of the Invention (Technical Field)

The present invention relates to methods for determination of parameters in lithography devices and applications by analysis of the variation in measurements of multiple diffracting structures located in different fields on a wafer, including determination of center of focus in lithography applications, such as for photoresist lithographic wafer processing, and methods of process and quality control using such determinations.

2. Background Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Lithography has a variety of useful applications in the semiconductor, optics and related industries. Lithography is used to manufacture semiconductor devices, such as integrated circuits created on wafers, as well as flat-panel displays, disk heads and the like. In one application, lithography is used to transmit a pattern on a mask or reticle to a resist layer on a substrate through spatially varying light. The resist layer is then developed and the exposed pattern is either cleaned away (positive resist) or remains (negative resist) to form a three dimensional image pattern in the resist layer. However, other forms of lithography are employed in addition to photoresist lithography.

In one form of lithography, particularly used in the semiconductor industry, a wafer stepper is employed, which typically includes a reduction lens and an illumination light source, a wafer stage, a reticle stage, wafer cassettes and an operator workstation. Modern stepper devices employ both positive and negative resist methods, and utilize either the original step-and-repeat format or a step-and-scan format, or both.

Exposure and focus determine the quality of the image pattern that is developed, such as in the resist layer utilizing photoresist lithography. Exposure determines the average energy of the image per unit area and is set by the illumination time and intensity. Focus determines the decrease in variation relative to the in-focus image. Focus is set by the position of the surface of the resist layer relative to the focal plane of the imaging system.

Local variations of exposure and focus can be caused by variations in the resist layer thickness, substrate topography, and lithography tool focus drift. Because of possible variations in exposure and focus, image patterns generated through lithography require monitoring to determine if the patterns are within an acceptable tolerance range. Focus and exposure controls are particularly important where the lithographic process is being used to generate sub-micron lines.

A variety of methods and devices have been used to determine focus of stepper and similar lithography tools. Scanning electron microscopes (SEM) and similar devices are employed. However, while SEM metrology can resolve features on the order of 0.1 microns, the process is costly, requires a high vacuum chamber, is relatively slow in operation and is difficult to automate. Optical microscopes can be employed, but do not have the required resolving power for sub-micron structures. Other methods include the development of specialized targets and test masks, such as are disclosed in U.S. Pat. Nos. 5,712,707, 5,953,128, and 6,088,113. Overlay error methods are also known, as disclosed in U.S. Pat. No. 5,952,132. However, these methods still require use of SEM, optical microscopes or similar direct measurement devices.

A variety of scatterometer and related devices and measurements have been used for characterizing the microstructure of microelectronic and optoelectronic semiconductor materials, computer hard disks, optical disks, finely polished optical components, and other materials having lateral dimensions in the range of tens of microns to less than one-tenth micron. For example, the CDS200 Scatterometer, made and sold by Accent Optical Technologies, Inc., is a fully automated nondestructive critical dimension (CD) measurement and cross-section profile analysis system, partially disclosed in U.S. Pat. No. 5,703,692. This device can repeatably resolve critical dimensions of less than 1 nm while simultaneously determining the cross-sectional profile and performing a layer thickness assessment. This device monitors the intensity of general diffracted light, which may include but is not limited to the intensity a single diffraction order as a function of the angle of incidence of the illuminating light beam. The intensity variation of the $0^{th}$ or specular order as well as higher diffraction orders from the sample can be monitored in this manner, and this provides information that is useful for determining the properties of the sample target which is illuminated. Because the process used to fabricate the sample target determines the properties of a sample target, the information is also useful as an indirect monitor of the process. This methodology is described in the literature of semiconductor processing. A number of methods and devices for scatterometer analysis are taught, including those set forth in U.S. Pat. Nos. 4,710,642, 5,164,790, 5,241,369, 5,703,692, 5,867,276, 5,889,593, 5,912,741, and 6,100,985.

Another technique to determine best focus uses a specially designed reticle based upon phase shift technology (R. Edwards, P. Ackmann, C. Fischer, "Characterization of Autofocus Uniformity and Precision on ASML Steppers using the Phase Shift Focus Monitor Reticle," *Proc. SPIE* Vol. 3051, pp. 448–455, 1997). As the features are shot further away from best focus, the images printed from the reticle become more asymmetric and have more lateral image displacement. These images can be analyzed using image-based metrology tools, such as those used for overlay measurements.

Another technique to determine best focus is the line-shortening technique, also known as 'schnitzlometry' (C. P. Ausschnitt, M. E. Lagus, "Seeing the forest for the trees: a new approach to CD control," *Proc. SPIE* Vol. 3332, pp. 212–220, 1998). The method uses relatively large CD (~3 microns) line/space arrays, where two arrays are placed next to each other. As the structures are printed through focus and/or dose, the lines themselves shorten and the space between the arrays broadens. This space can be measured using image-based metrology tools such as those used for overlay measurements.

One of the more widely used techniques for determination of best focus is the so-called "Bossung plot" method. When a CD metrology tool such as a CD-SEM or scatterometer measures CD on a selected feature printed through focus, the resulting trend is usually parabolic. Fitting a parabolic curve to the CD trend and determining where the slope of the curve is zero identifies best focus. These curves are known as Bossung plots. One advantage to the Bossung method is that the actual CD of the process is quantified in addition to the best focus condition. However, the method is not always robust for certain process conditions which makes it difficult to determine best focus and difficult to implement in an automated manner. Furthermore, when the method is used with a CD-SEM, the measurement may be influenced by changes to the sidewall angle of the lines and hence produce a biased result.

Scatterometers and related devices can employ a variety of different methods of operation. In one method, a single, known wave-length source is used, and the incident angle Θ is varied over a determined continuous range. In another method, a number of laser beam sources are employed, optionally each at a different incident angle Θ. In yet another method, an incident broad spectral light source is used, with the incident light illuminated from some range of wavelengths and the incident angle Θ optionally held constant. Variable phase light components are also known, utilizing optics and filters to produce a range of incident phases, with a detector for detecting the resulting diffracted phase. It is also possible to employ variable polarization state light components, utilizing optics and filters to vary the light polarization from the S to P components. It is also possible to adjust the incident angle over a range φ, such that the light or other radiation source rotates about the target area, or alternatively the target is rotated relative to the light or other radiation source. Utilizing any of these various devices, and combinations or permutations thereof, it is possible and known to obtain a diffraction signature for a sample target.

Besides scatterometer devices, there are other devices and methods capable of determining the diffraction signatures at the $0^{th}$ order or higher diffraction orders using a light-based source that can be reflected off of or transmitted through a diffraction structure, with the light captured by a detector. These other devices and methods include ellipsometers and reflectometers, in addition to scatterometers. It is further known that non-light-based diffraction signatures may be obtained, using other radiation sources as, for example, X-rays.

A variety of sample targets are known in the art. A simple and commonly used target is a diffraction grating, essentially a series of periodic lines, typically with a width to space ratio of between about 1:1 and 1:3, though other ratios are known. A typical diffraction grating, at for example a 1:3 ratio, would have a 100 nm line width and a 300 nm space, for a total pitch (width plus space) of 400 nm. The width and pitch is a function of the resolution of the lithographic process, and thus as lithographic processes permit smaller widths and pitches, the width and pitch may similarly be reduced. Diffraction techniques can be employed with any feasible width and pitch, including widths and/or pitches substantially smaller than those now typically employed. Bi-periodic and other multi-periodic structures are also known, such as those disclosed in U.S. patent application Publication No. US 2002/0131055, published Sep. 19, 2002. Three-dimensional gratings or structures are also known, including those disclosed in U.S. Pat. No. 6,429,930. Thus diffracting structures may possess more than one period, or may be made up of elements other than lines and spaces, such as holes, squares, posts or the like. It is further known that diffraction from a non-periodic structure, such as an isolated feature or series of features, may also employed for the method and claims discussed herein.

Diffraction structures are typically dispersed, in a known pattern, within dies on a wafer. It is known in the art to employ multiple dies (or exposure fields) on a single wafer. Each diffraction structure may be made by lithographic means to be at a different focus, such as by employing a different focus setting or a different exposure setting or dose. It is also known that center of focus may be determined using scatterometry and diffraction structures by comparing diffraction signatures from diffraction structures at different focus positions to a theoretical model library of diffraction signatures. The actual diffraction signatures are compared to the model, and CD values are derived. The CD value thus obtained is plotted against focus and the results fit to a parabolic curve. This Bossung plot method, discussed above, has significant inherent limitations.

U.S. Pat. Nos. 6,429,930 and 6,606,152, by the same inventors as this application, teach a method of measuring parameters relating to a lithography device utilizing the steps of providing a substrate comprising a plurality of diffraction gratings formed on the substrate by lithographic process utilizing the lithography device, the diffraction gratings comprising a plurality of spaced elements; measuring a diffraction signature for at least three of the plurality of diffraction gratings by means of a radiation source-based tool; and determining the differences between the diffraction signatures to determine a desired parameter of said lithography device. In this method, the substrate can include a wafer. The method can further include forming the plurality of diffraction gratings utilizing the lithography device at different known focus settings, and determining the two adjacent focus setting diffraction gratings wherein the difference between the diffraction signatures is less than the difference of the diffraction signatures between other adjacent focus setting diffraction gratings, whereby the parameter is the center of focus of the lithography device. That is, as best focus is reached, the difference between diffraction signatures between adjacent focus steps will minimize.

International Patent Application PCT/US02/32394, by the same inventors as this application, teaches a method of measuring parameters relating to a lithography device comparing a measured diffraction signature from a diffraction structure to a library of theoretical models; the cross-section of the deposited diffraction structure is determined by that of the model which most closely matches the obtained diffraction signature. This is repeated for diffraction structures which were made with varying focus. A wide variety of parameters, calculated from, for example, CD, sidewall, or resist thickness, may be substituted for the cross-section; these parameters may be areas, volumes, or non-geometric. The ratio of cross-section to the maximum cross-section area obtained in the focus trend, the numerical difference between cross-sections for structures with adjacent focus steps, or the cross-section itself may be plotted versus focus. In these cases, the center of focus is determined by the point at which the curve, generally fit to a parabola, has a slope of zero. In the last case, curve-fitting is not required; center of focus is at the minimum or maximum value of the cross-section.

SUMMARY OF THE INVENTION
(DISCLOSURE OF THE INVENTION)

The present invention is a method of measuring parameters relating to a lithography device comprising the steps of providing a substrate, preferably a semiconductor wafer, comprising a plurality of fields, each field having been exposed at a different focus value and comprising a plurality of diffraction structures formed on the substrate by a lithographic process utilizing the lithography device; measuring a diffraction signature for each of a plurality of the diffraction structures in a plurality of fields by means of a radiation source-based tool; determining for each field the variability of measured diffraction signatures obtained from the plurality of diffraction structures located within that field; and comparing the variabilities associated with the fields to determine a desired parameter of the lithography device. The diffraction structures may be single period, bi-periodic, multi-periodic, or non-periodic structures, including gratings.

The radiation source-based tool preferably comprises a light source-based tool, preferably comprising one or more incident laser beam sources, an optical system focusing the laser beams and scanning through some range of incident angles, and a detector for detecting the resulting diffraction signature over the resulting measurement angles. The tool optionally comprises an angle-resolved scatterometer. Alternatively, the tool comprises an incident broad spectral light source, an optical system focusing the light and illuminating through some range of incident wavelengths, and a detector for detecting the resulting diffraction signature over the resulting measurement wavelengths. The tool optionally comprises an incident light source, components for varying the amplitude and phase of the S and P polarizations, an optical system focusing the light and illuminating over some range of incident phases, and a detector for detecting the phase of the resulting diffraction signature.

Measuring the diffraction signature according to the above method optionally comprises phase measurement by means of either a broad spectral (or, alternatively, single wavelength) radiation source-based tool source, operating at a fixed angle, a variable angle of incidence $\Theta$ or a variable angle of sweep $\phi$, or alternatively a multiple discrete wavelength radiation source-based tool source. The diffraction signature is optionally a reflective, transmissive, specular order, or higher order diffraction signature, and is optionally a measurement of general light scatter or diffraction. The desired parameter is preferably the center of focus, or optionally dose, and is preferably determined by a value of the desired parameter associated with the field having a minimum variability of the diffraction signatures.

The determining step optionally comprises measuring for each field the range of intensities of the diffraction signatures obtained from the plurality of measured diffraction structures located within that field, or alternatively calculating a statistical measure of the variability, such as the root mean square error of the diffraction signatures.

Alternatively, the determining step comprises providing a library of theoretical diffraction signatures generated from theoretical diffraction structures; determining in the library a best match theoretical diffraction signature for each measured diffraction signature; associating a chosen feature of the best match theoretical diffraction signature with the measured diffraction signature; and determining for each field the variability of the chosen feature associated with the plurality of diffraction structures located within that field. The chosen feature is preferably CD, or alternatively a cross-section area, a cross-section volume, or a product of two or more features of the theoretical diffraction structure providing the matching theoretical diffraction signature. The determining step optionally comprises measuring for each field the range of the chosen features associated with the plurality of measured diffraction structures located within that field, or alternatively comprises calculating a statistical measure of the variability, such as the standard deviation of the chosen features.

The method optionally comprises forming the plurality of diffraction structures at known different focus settings and known different dose settings and determining the effect of dose on focus, wherein the plurality of diffraction structures optionally comprise sets of the same known different focus setting diffraction structures, the sets varying by different known dose settings. The diffractions structures of the above method optionally comprise latent image diffraction structures, and the substrate optionally has not been subjected to a development process.

The present invention is further a method of process control for center of focus in a lithography device, the method comprising the steps of determining the center of focus of the lithography device according to the above method; and adjusting the focus setting of the lithography device to the determined center of focus, optionally utilizing a computer-based control system or an autofocus control system, wherein at least one input to the autofocus control system comprises a measure relating to a minimum variability. The variability of measured diffraction signatures obtained from the plurality of diffraction structures located within a selected field is preferably measured over time, and the selected field preferably was previously determined to be at the center of focus. Preferably, the focus of the lithography device is adjusted if the variability exceeds a predetermined control limit.

The present invention is also a method of process control in a lithography device, the method comprising the steps of exposing a plurality of diffraction structures in a similarly positioned and exposed field on a series of wafers with the lithography device; measuring a diffraction signature for each of the plurality of diffraction structures in each similarly positioned and exposed field on the series of wafers by means of a radiation source-based tool; determining for each wafer the variability of measured diffraction signatures obtained from the plurality of diffraction structures in the field; and comparing the variabilities associated with the wafers to control a desired parameter of the lithography device. The method preferably comprises the additional step of adjusting at least one desired parameter of the lithography device in response to the compared variabilities associated with the wafers. The variabilities are preferably compared to an empirically or theoretically determined variability limit. The at least one desired parameter preferably comprises focus or dose. The diffraction structures are preferably single period, bi-periodic, multi-periodic, or non-periodic structures, such as gratings. The wafers preferably comprise semiconductor wafers.

The radiation source-based tool preferably comprises a light source-based tool, preferably comprising one or more incident laser beam sources, an optical system focusing the laser beams and scanning through some range of incident angles, and a detector for detecting the resulting diffraction signature over the resulting measurement angles. The tool optionally comprises an angle-resolved scatterometer. Alternatively, the tool comprises an incident broad spectral light source, an optical system focusing the light and illuminating through some range of incident wavelengths, and a detector for detecting the resulting diffraction signature over the resulting measurement wavelengths. The tool optionally comprises an incident light source, components for varying the amplitude and phase of the S and P polarizations, an optical system focusing the light and illuminating over some range of incident phases, and a detector for detecting the phase of the resulting diffraction signature.

Measuring the diffraction signature according to the above method optionally comprises phase measurement by means of either a broad spectral (or, alternatively, single wavelength) radiation source-based tool source, operating at a fixed angle, a variable angle of incidence $\Theta$ or a variable angle of sweep $\phi$, or alternatively a multiple discrete wavelength radiation source-based tool source. The diffraction signature is optionally a reflective, transmissive, specular order, or higher order diffraction signature, and is optionally a measurement of general light scatter or diffraction. The desired parameter is preferably the center of focus, or optionally dose, and is preferably determined by a value of the desired parameter associated with the field having a minimum variability of the diffraction signatures.

The determining step optionally comprises measuring for each wafer the range of intensities of the diffraction signatures obtained from the plurality of measured diffraction structures located within that field on that wafer, or alternatively calculating a statistical measure of the variability, such as the root mean square error of the diffraction signatures.

Alternatively, the determining step comprises providing a library of theoretical diffraction signatures generated from theoretical diffraction structures; determining in the library a best match theoretical diffraction signature for each measured diffraction signature; associating a chosen feature of the best match theoretical diffraction signature with the measured diffraction signature; and determining for each wafer the variability of the chosen feature associated with the plurality of diffraction structures located within the field on that wafer. The chosen feature is preferably CD, or alternatively a cross-section area, a cross-section volume, or a product of two or more features of the theoretical diffraction structure providing the matching theoretical diffraction signature. The determining step optionally comprises measuring for each wafer the range of the chosen features associated with the plurality of measured diffraction structures located within the field on that wafer, or alternatively comprises calculating a statistical measure of the variability, such as the standard deviation of the chosen features. The diffraction structures optionally comprise latent image diffraction structures, and the wafer optionally has not been subjected to a development process.

A primary object of the present invention is to provide a method for measuring parameters relating to a lithography device without the use of optical, SEM or similar microscopy metrology tools.

Another object of the present invention is to provide a method for determining center of focus of a lithography device by analyzing the best match theoretical diffraction signatures of a series of fields of different focus diffraction structures, including but not limited to diffraction gratings, and utilizing the intra-field variability of the best match structures to determine center of focus.

Another object of the present invention is to provide a method for determining or measuring parameters associated with a lithography device, including center of focus, by obtaining diffraction signatures of a number of same focus structures within a number of different focus fields utilizing either reflective or transmissive diffraction, and determining the intra-field variance between such diffraction signatures or the intra-field variances of a chosen feature derived from a theoretical model providing a best match theoretical diffraction signature.

Another object of the present invention is to provide a method for determining or measuring parameters associated with a lithography device, including center of focus, by obtaining a diffraction signature utilizing any method to create a diffraction signature, including but not limited to reflective or transmissive angle-resolved, variable wavelength, variable phase, variable polarization state or variable orientation diffraction, or a combination thereof, of the $0^{th}$ or specular diffraction order or any higher orders or any diffracted or scattered light.

Another object of the present invention is to provide a method for determining or measuring parameters associated with a lithography device by means of any order of diffraction signature of different focus fields within a wafer or other substrate, including the $0^{th}$ or specular order or any higher order diffraction, either positive or negative, or any diffracted or scattered light.

A primary advantage of the present invention is that it permits measuring parameters relating to a lithography device without the use of optical, SEM or similar microscopy metrology tools.

Another advantage of the present invention is that it provides a method and device that permits obtaining results, including center of focus, in a lithography device, such as a stepper, in a shorter period of time and at lower cost than conventional and known methods.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings:

FIG. 1A depicts a wafer with a number of fields exposed at differing focus values;

FIG. 1B depicts one of the fields of FIG. 1A comprising a number of diffraction structures;

FIG. 2 is a graph of the standard deviation of the measured CDs of the diffraction structures for each field;

Figure 3A:
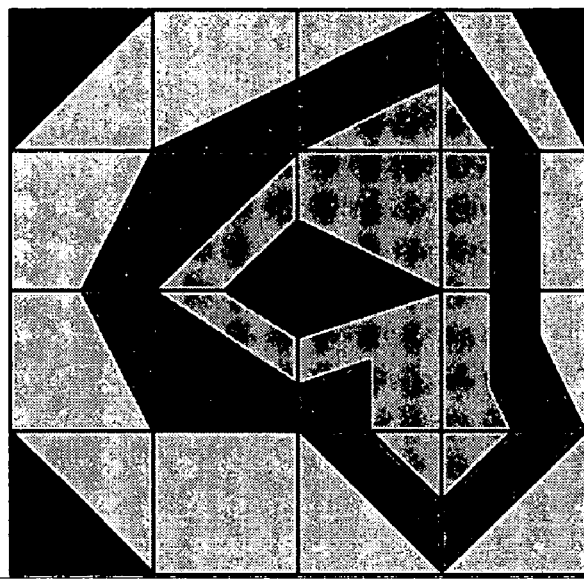
FIGS. 3A–3E graphically depict the variation in CD for various fields according to Example 1 of the present invention.
Figure 3B:
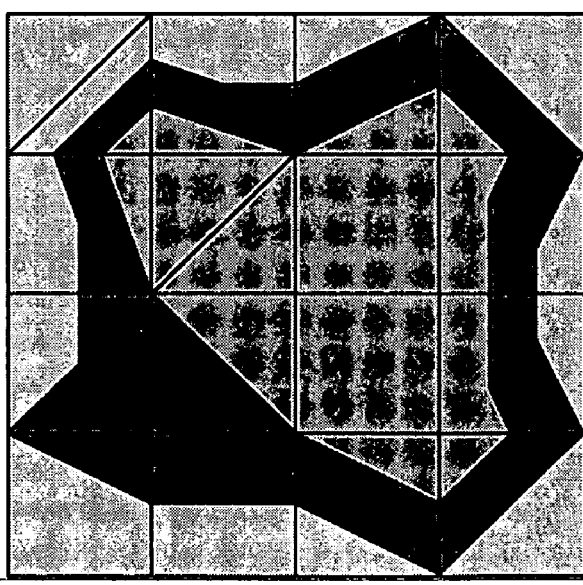
Figure 3C:
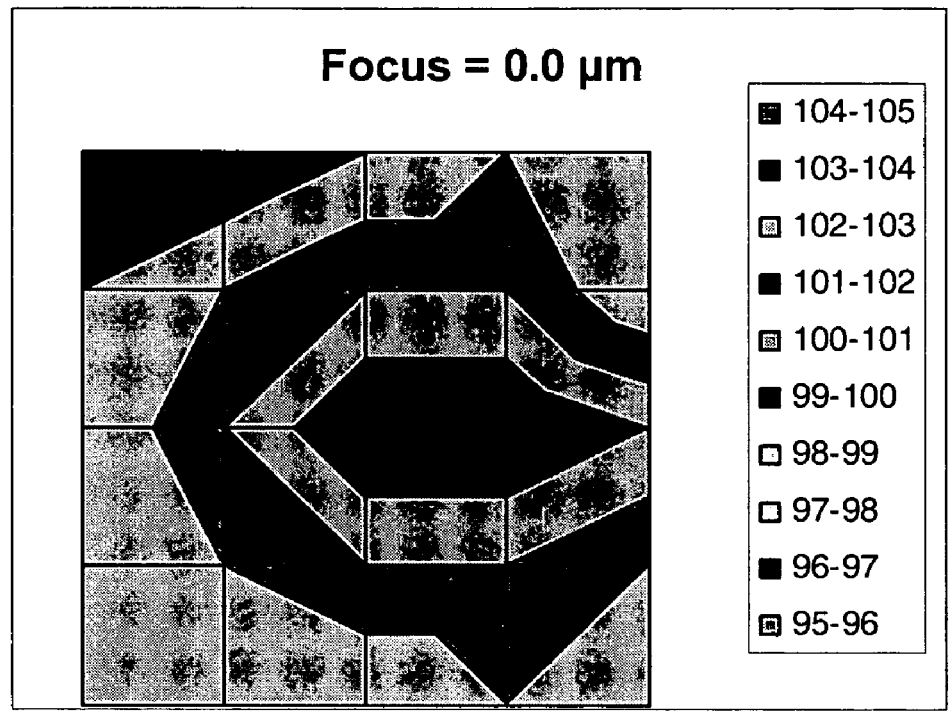
Figure 3D:
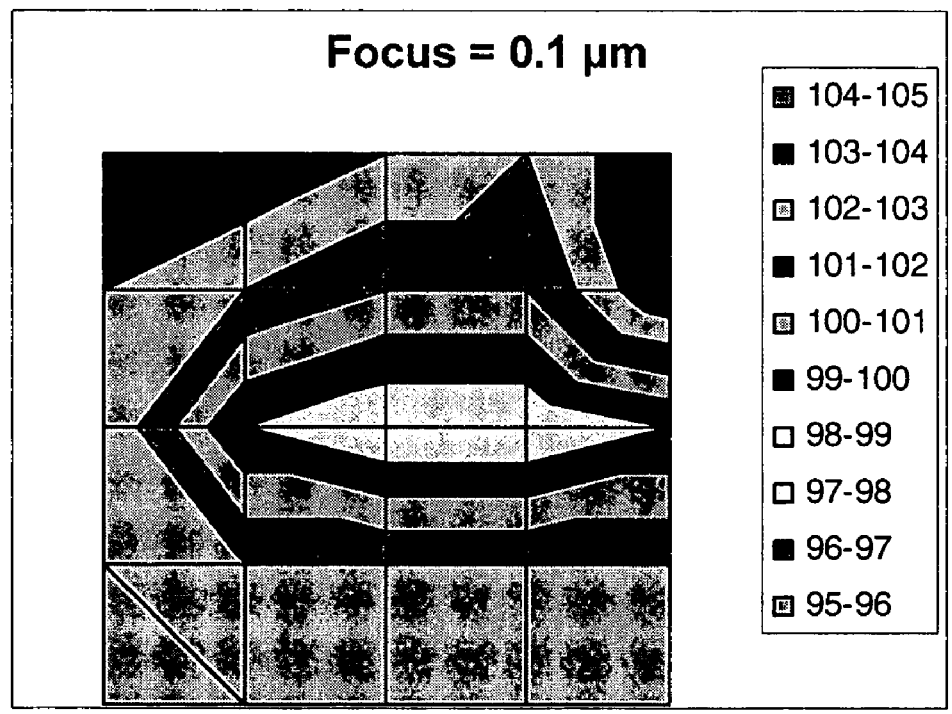
Figure 3E:
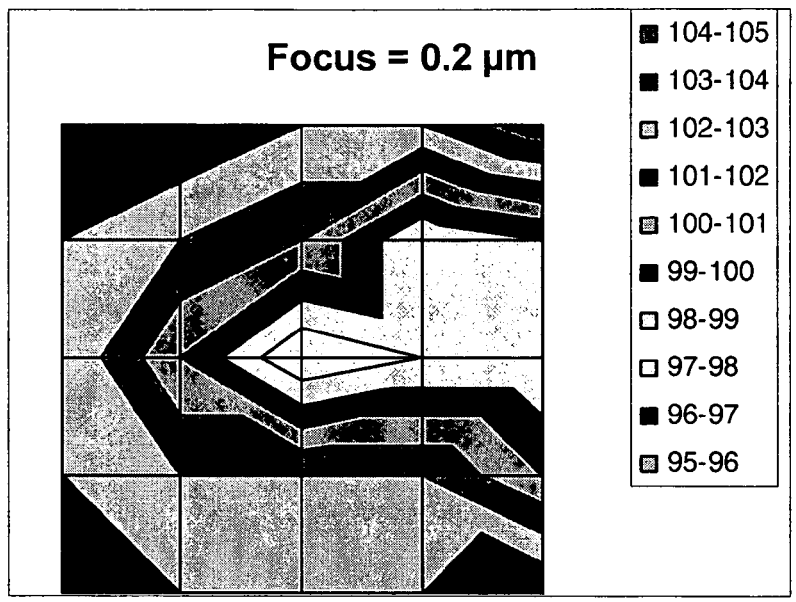

DESCRIPTION OF THE PREFERRED EMBODIMENTS (BEST MODES FOR CARRYING OUT THE INVENTION)

The present invention provides methods and devices for measuring parameters relating to a lithography device, and in a preferred embodiment, for determining the center of focus of a lithography device. Determination of the center of focus for a fixed dose during the photoresist development step in wafer processing is critical. Furthermore, dose variations can compound the difficulty in determining this center. The lenses that are used in lithography tools have a very limited depth of focus, so utmost precision is necessary. Lenses that are in focus will yield sharper printed photoresist images, and lack of focus will result in misdeveloped photoresist features, and generally poorer process yields. Being at the center of focus, or best focus, improves process repeatability and stability. A method of determining center of focus is disclosed in this application which utilizes variability analysis; in brief, center of focus is determined by diffracting structure field uniformity. The invention further includes manufacturing process monitoring based on diffraction signature uniformity.

Before proceeding to further describe the invention, the following definitions are given.

As used throughout the specification and claims, variability or variation means the extent that values of a quantity or parameter measured from, or calculated for, each of a desired group of items, including but not limited to diffraction structures, differ from one another. Variability or variation is the opposite of uniformity, and the terms may be used as such. Determining, measuring, calculating, or comparing variability is therefore synonymous with determining, measuring, calculating or comparing uniformity. As an example, the term "minimum variability" is synonymous with the term "maximum uniformity", and those two terms are used interchangeably throughout the specification and claims.

A lithography device refers to any device that utilizes an image, such as a mask, to transfer a pattern to and optionally into a substrate. This thus includes conventional optical lithography, such as photoresist lithography, but also includes other methods of lithography. In photoresist lithography, also called photolithography, optical methods are used to transfer circuit patterns from master images, called masks or reticles, to wafers. In this process, one or more specialized materials called resists are coated on the wafers on which the circuits are to be made. A resist coat is applied as required, and as required the wafer is further processed, such as by a softbake. Either positive or negative photoresist materials may be employed. Positive resists are normally insoluble in chemicals used as resist developers, but become soluble by exposure to light. Negative resists are normally soluble in chemicals used as resist developers, but become insoluble by exposure to light. By exposing the resist selectively in some areas but not others, the pattern of the circuit or other structure is created in the resist film. In optical lithography, the selective exposure is accomplished by imaging of a mask, typically by shining light onto the mask and projecting the transmitted image onto the resist film.

The lithography devices referenced in this invention include steppers and scanners, also known as wafer steppers or wafer scanners, which are used to project the image of a circuit or other structure from a photomask onto a resist-coated wafer. A stepper or scanner typically includes reduction lens and illuminator, excimer laser light source, wafer stage, reticle stage, wafer cassettes and an operator workstation. Steppers and scanners employ both positive and negative resist methods, and utilize either a step-and-repeat format or a step-and-scan format, or combination thereof.

There is employed in the practice of this invention a wafer or other substrate on which is posited a series of diffraction structures by means of a lithographic device. In its simplest terms, a diffraction structure is any structure or image made by lithographic means which generates a spatial variation of the refractive index relative to an incident illumination. This change in refractive index can be either due to a physical difference or a chemical difference. Physical differences include photoresist or other lithographically generated changes, such as utilizing a material with one refractive index coupled with air, such as ordinary scored optical diffraction gratings, or a material coupled with a different material. Chemical differences include wafers with photoresist exposed diffraction structures, such as gratings, where the resist has not yet been developed. In this case all of the resist is still present, but the portions that have been exposed have a different refractive index than the non-exposed resist portions, thereby creating a diffraction structure consisting of periodic variations of refractive index in the resist. The periodic difference is obtained by the periodicity of structural or chemical elements. A diffraction structure may have a single period, may be bi-periodic, or may be multi-periodic, or may not possess any periodicity, since diffraction from single features is possible. This thus includes conventional diffraction gratings consisting of a series of parallel lines, structures such as a three-dimensional array of posts or holes, wherein there is periodicity in both in the X direction and Y direction, and structures without periodicity in either the X or Y directions. A diffraction structure without periodicity may be, for example, a single line, a larger single rectangular structure, or a more complicated real device structure. Similarly, the aforementioned diffraction structures may not be "fully periodic" (where the structure is repeated multiple times (generally 10 or more) under the illumination beam, but may repeat only a few times (for example, two or three times). Diffraction structures thus include photoresist gratings, etched film stack gratings, metal gratings and other gratings known in the art. A diffraction grating typically has a line width to space ratio of between about 1:1 to 1:3, though other ratios may be employed. A typical diffraction grating, at for example a 1:3 ratio, could have a 100 nm line width and a pitch of 400 nm. The width and pitch can be significantly smaller, depending in part on the resolution of the lithographic device.

In the practice of this invention, a diffraction structure is used to generate a diffraction signature. A diffraction signature can be generated by any of a number of instruments, such as scatterometers, ellipsometers or reflectometers, using optical techniques such as scatterometry, interferometry, polarimetry, reflectometry, spectroscopic ellipsometry or spectroscopic reflectometry, and using any technique, such as angular or spectral analysis. Any device employing radiation to generate a diffraction signature is referred to herein as a radiation source-based tool. Typically a visible radiation source-based tool, such as a light source-based tool, is employed, but the radiation source may be other than visible radiation, such as an X-ray source. In one embodiment, the diffraction signature is created by a reflective mode, wherein the radiation, such as light, is reflected. Thus a diffraction signature may be generated by means of an angle-resolved scatterometer, wherein a single known wavelength source is used, and the incident angle $\Theta$ is varied over a determined continuous range. The resulting diffraction signature can be depicted as the intensity of light plotted against the incident and reflective angle $\Theta$. In another method, a number of laser beam sources are employed, optionally each at a different incident angle $\Theta$. In yet another method, an incident broad spectral light source is used, with the incident light illuminated from some range of wavelengths and the incident angle $\Theta$ optionally held constant. Variable phase light sources are also known, utilizing a range of incident phases, with a detector for detecting the resulting diffracted phase. Variable polarization light sources are also known, utilizing a range of polarization from the S to P components or the P to S components. It is also possible to adjust the incident angle over a range $\phi$, such that the light source rotates about the diffraction structure, or alternatively the diffraction structure is rotated relative to the light source. Utilizing any of these various devices, and combinations or permutations thereof, it is possible and known to obtain a diffraction signature for a given diffraction structure. In general, the detected light intensity can be plotted against the at least one variable parameter, such as angle of incidence $\Theta$, wavelength of incident light, phase of incident light, angle of sweep $\phi$ or the like. The diffraction signature may represent the $0^{th}$ or specular diffraction order, or may represent any higher diffraction order, or may be a measurement of the general light diffraction or scatter. It is also possible and contemplated that a transmissive mode may be employed to generate a diffraction signature, such as by use of an X-ray radiation source as a component of the radiation source-based tool.

In one embodiment of the invention, a theoretical library of diffraction structures and corresponding theoretical diffraction signatures is generated, and theoretical diffraction signatures based on the theoretical diffraction structures are compared to the measured diffraction signature. This may be done by any number of different methods. In one approach, an actual library of theoretical output signals are generated based on assigned parameters for variable features. This library may be generated prior to actual measurement of a diffraction signature or may be generated in a process of matching the measured diffraction signature to a theoretical diffraction signature. Thus as used herein a theoretical library includes both a library generated independent of the measured diffraction signature and a library generated based on a theoretical "best guess" of the geometry of the measured structure and calculation of the resulting theoretical diffraction signature, with iterative comparison to changed features to determine a best match. The theoretical library of diffraction signatures may also be generated empirically, such as by a collection of diffraction signatures of diffraction structures with dimensions measured by an alternative means. The library may optionally be pruned by removing signals that may be accurately represented via interpolation from other signals in the reference set. An index of the library can similarly be generated by correlating each signature with one or more indexing functions and then ordering the index based on the magnitude of the correlation. Construction or generation of libraries of this type, and methods for optimization thereof, are well known in the art. In one approach, a rigorous, theoretical model based on Maxwell's equations is employed to calculate a predicted optical signal characteristic of the diffraction structure, such as the diffraction signature, as a function of diffraction structure parameters. In this process, a set of trial values of the diffraction structure parameters is selected. Then, based on these values a computer-representable model of the diffraction structure, including its optical materials and geometry, is constructed. The electromagnetic interaction between the diffraction structure and illuminating radiation is numerically simulated to calculate a predicted diffraction signature. Any of a variety of fitting optimization algorithms may be employed to adjust the diffraction structure parameter values, with the process iteratively repeated to minimize discrepancy between the measured and predicted diffraction signature, thereby obtaining the best match. U.S. Published patent application No. US 2002/0046008 discloses one database method for structure identification, while U.S. Published patent application No. US 2002/0038196 discloses another method. Similarly, U.S. Published patent application No. US 2002/0135783 discloses a variety of theoretical library approaches, as does U.S. Published patent application No. US 2002/0038196. Grating or diffraction structure features that may be utilized in a theoretical library include any feature that may be modeled, including factors such as:

CDs at the bottom and/or top of the structure

Height or thickness, such as height or thickness of a line, post or other structure Total height of the region defined by a diffraction signature Shape of a structure, such as rectangular, trapezoidal, triangular, round or other geometric shapes Radius of curvatures at the bottom and/or top of a structure or region Sidewall Period of a grating Line or other structure width Materials parameters of the structure, including parameters of various layers thereof Materials parameters of the substrate on which a structure is posited, such as film thickness and index of refraction of films underneath the structure Various weighted or average values, such as CD at a specified location, values weighted by relative contributions of the structure and substrates, or the like Underlying thin film thickness and optical properties of the materials generally will not result in substantial variation in the theoretical library models across focus. However, depending on the choice of scatterometer, configuration and theoretical model, changes in focus may result in changes in these properties. It may thus readily be seen that the theoretical library may incorporate thin film thickness and optical constants in the determined cross-section. This may be as simple as adding the thin film thickness cross-section over an equivalent periodicity to the grating cross-section area, or may be more complicated, such as weighting the contribution of the grating and thin film cross-section areas by the material optical n & k constants. The theoretical model may also take into account underlying films and patterns.

In one embodiment of the invention, a cross-section of the theoretical diffraction structure that has the best match theoretical diffraction signature compared to the measured diffraction signature is calculated. A cross-section is, within the meaning of this invention, the product of at least two diffraction structure features of the best match structure. In one embodiment, the cross-section is a cross-section area, such as the product of CD and height. In another embodiment, the cross-section is a cross-section volume, such as the product of CD, height and shape of a structure. However, as used herein the cross-section need not be a geometrically defined shape; that is, the cross-section can be the product of any two or more diffraction structure features, including but not limited to those listed above. In one embodiment, the cross-section includes CD and at least one additional diffraction structure feature. As used herein, a product of at least two diffraction structure features, is any mathematical operation or manipulation of the at least two features, including but not limited to a mathematical operation including multiplication, and optionally at least one second mathematical operation.

A wide variety of theoretical model profiles can be used to determine the cross-section area. For example, the cross-section grating area for a rectangular grating is defined by the formula:

$$\text{Cross-Section Area} = H \cdot W \quad (1)$$

where H is the grating height and W is the grating width. To improve the accuracy in determining center of stepper focus, more detailed theoretical models may be used. One such model is a trapezoid, which adds the dimension of sidewall angle. The equation to determine the cross-section of the trapezoidal grating is $$\text{Cross-Section Area} = H \cdot (W - H/\tan A) \quad (2)$$

where H is the grating height, W is the width at the bottom of the grating, and A is the sidewall angle of the trapezoid. Other, more complex shapes such as a trapezoid with rounded edges, gaussian or sigmoidal profile, or other custom profile designated by the user, may also be used to generate the theoretical model. With more complex shapes more complex equations are needed to express the grating shape in terms of cross-section area.

Three-dimensional structures may also be analyzed in a similar method. For three-dimensional structures one measure of the cross-section is a cross-section volume. For example, a simple contact hole model assuming a perfect circle profile in X-axis and Y-axis and a constant sidewall at 90 degrees along the Z-axis may have its cross-section calculated as a cylinder, thereby yielding a cross-section volume.

It may further be seen that entirely non-geometric cross-sections may be employed. Thus, the cross-section may be the product of one feature, such as CD, and one or more additional features, such as for example materials parameters, weighted or average values, angular measures, optical properties, curvatures, or the like. The resulting products may be employed in similar fashion to cross-section areas or volumes.

The best match or match of the cross-section of a theoretical diffraction signature to the measured diffraction signature can be calculated by any means known in the art. In one embodiment, it can include a match of the measured diffraction signature to discrete and existing theoretical diffraction signatures contained in an existing library, such as through use of various matching algorithms, whereby utilizing defined constraints a best match is selected. In another embodiment, a best match can include library interpolations to obtain a theoretical diffraction signature, even though such theoretical diffraction signature may not exist prior to interpolation. It can further include averaging and related models to report a theoretical diffraction signature based on sampling of theoretical diffraction signatures contained in a library. Thus any method or technique of identifying or matching a reported diffraction signature to a theoretical diffraction signature, however obtained, may be employed herein to determine a match or best match.

The diffraction structures are typically created in a resist material by preparing masks with opaque and transparent areas corresponding to the desired shape, size and configuration of the desired diffraction structure. A source of radiation is then applied on one side of the mask, thereby projecting the mask shape and spaces onto the resist layer, the resist layer being on the opposite side of the mask. One or more lens or other optical systems may be interposed between the mask and the resist layer, and also optionally between the radiation source and the mask. When exposed to radiation or energized at sufficient levels to effect a change in the resist, a latent image is formed in the resist. The latent images, representing a chemical change in the resist material, result in changes in reflectivity of the resist layer, and thus may be employed to generate a diffraction signature as set forth above. In one embodiment, the wafer with latent images in the resist may be subjected to a post-exposure bake, used to drive additional chemical reactions or to diffuse components within the resist layer. In yet another embodiment, the resist may be developed by a development process, optionally a chemical development process, whereby a portion of the resist is removed, the portion determined by whether a positive resist or negative resist was employed. The development process is also referred to as an etching process, resulting in etched areas or spaces of the resist layer, and optionally the substrate material, such as other films, on which such resist layer is posited.

In the methods and devices of this invention, the diffraction structure may be exposed but not developed, or may alternatively be developed. Similarly, while the foregoing generally describes a conventional method of generating a diffraction structure, any method may be employed, including use of phase shift masks, any of a variety of sources of radiation, including electron beam exposure, and the like.

Focus is a critical parameter in any lithography device, including a stepper or similar lithography device. Focus and depth-of-focus are functions of dose, or quanta of radiation energy, and focus, or distance from the lens to the target. The resulting imaging must be good for all points within a given exposure field, thereby resulting in a definable usable depth-of-focus. However, factors other than dose and focus affect the focus and depth-of-focus, including astigmatism, field curvature, lens quality, orientation of the wafer stage in the X- and Y-axes, and the like. Typical production wafer steppers have a resolution of from about 0.15 to about 1.25 microns, and a usable depth-of-focus of from about 0.40 to about 1.50 microns.

Determination of the center of focus for a fixed dose is thus critical in efficient operation of a lithography device, such as for a stepper during the photoresist exposure step in wafer processing. Dose variations compound the difficulty in determining this center. The lenses that are used in steppers and other lithographic devices have a very limited depth of focus, so utmost precision is necessary. Lenses that are in focus will yield sharply printed photoresist images, and lack of focus will result in non-functional photoresist features. Being at the center of focus also significantly improves process repeatability. Once the center of focus is known and determined, any of a variety of different auto-focus systems or schemes may be employed for determining that the separation between the lens and the wafer is held constant. These systems include optical methods, such as employing reflected light, capacitance methods and pressure sensor methods, such as employing pressurized air. However, these systems and schemes are incapable of determining center of focus, but simply maintain the lens-to-wafer distance at a constant. In typical operations, the center of focus must be determined periodically, as often every six hours or less of operation of a lithography device.

Lens aberrations and distortions increase as one moves from the center of the lens outward to the edges. These aberrations and distortions become more prominent the further the optical system is from focus in either the positive or negative direction. Thus multiple diffraction structures distributed across the entire field of a lens which are shot at an identical focus value which is out of focus, will exhibit a greater variability than those shot in focus.

In a preferred embodiment, as shown in FIG. 1A, a series of spaced fields 20 is exposed or printed through focus, preferably by lithographic means using a wafer stepper at a fixed dose across a wafer or other substrate 10. Each field 20 is preferably exposed with a different focus value; the resulting series of focus values preferably includes the center of focus. In the example of FIG. 1A, the amount that the focus deviates from the zero focus position is denoted by the number displayed on each field 20. The initial zero focus position is arbitrarily chosen, or optionally is chosen to correspond to a physical dimension, such as the position of the top of the resist. Since best focus usually occurs when focusing some distance into the resist, the actual point of best focus, or center of focus, will most likely not correspond with the initial zero focus position. The actual displayed numbers are not to be construed as limiting. The focus may vary by an amount greater than +0.4 microns or less than −0.4 microns. The order of the numbers, i.e. which field is shot at which focus deviation, may similarly differ from that depicted in FIG. 1A.

Each field preferably consists of a plurality of spaced diffraction structures 30, 30' for example diffraction gratings, preferably distributed around each field. FIG. 1B depicts a field having twenty-five diffraction structures 30, 30' equally spaced in a 5×5 array; however, any number of structures may be employed, and their spacing does not have to be even across field 20. Optionally, the field may consist of one large grating where measurements as discussed below are made at several points within the large grating, or a combination of the two where there are several large gratings in the field where each large grating is sampled at various points within the grating. Diffraction structures 30, 30' consist of repeating or periodic structures or non-periodic features capable of diffracting radiation, and may either be two-dimensional, such as a conventional diffraction grating with lines and spaces, or three-dimensional, such as holes, posts or more complex structures. Preferably diffraction structures 30, 30' are artificial structures specifically used for the purposes of the present invention; however, it is possible that they actually comprise real structures which are being manufactured on each die on the wafer. Using a radiation source-based tool capable of scatterometric measurements, each diffraction structure 30, 30', or a determined sample thereof, is measured to obtain a diffraction signature at a fixed dose.

In a preferred embodiment, each diffraction signature is compared to a theoretical library of diffraction signatures, each with known features. A best match is found between each experimental diffraction signature and a theoretical diffraction signature, and a chosen feature associated with the best match theoretical model is assigned to each diffraction structure 30, 30'. The chosen feature may comprise a single feature, such as CD (measured, for example, in nanometers), or a combination of features to form a cross-section (as defined above). The chosen feature will be different for each diffraction structure 30, 30'. Preferably the 1-sigma standard deviation of the chosen features for diffraction structures 30, 30' within each field 20 is then calculated. A uniformity metric other than 1-sigma standard deviation may optionally be employed, including but not limited to the overall range (maximum minus minimum) of the chosen feature for each field, or other statistical or mathematical method for expressing variation.

The theoretical library, used to determine the cross-section, may employ a model with a simple shape such as a rectangle, or may employ more complex shapes such as a trapezoid, trapezoid with rounded edges, gaussian or sigmoidal profile or other custom profile designated by the user. The theoretical library may also take into account underlying films and patterns. The theoretically generated diffraction signatures, which have known features, are matched to the experimental data to obtain the theoretically predicted process features. More complex models can incorporate the optical properties of the diffraction structure, such as optical n and k values, as well as underlying film thicknesses, to make the focus metric a summation of the optical path.

The standard deviation of the chosen feature (or diffraction signature variability) for each field 20 is then plotted versus the relative focus of each field 20, as shown in FIG. 2. Although the chosen feature is in this case CD, any feature or combination of features may be chosen. The focus setting of the field having the minimum standard deviation of the chosen feature, i.e. the lowest variability (or maximum uniformity) of diffraction structures 30, 30', defines best focus, or center of focus. Optionally, a parabolic curve may be fit to the data plotted in FIG. 2, and the center of focus is determined by the minimum of the parabola, where the slope of the curve is zero. In that case, it is understood that various statistical or mathematical techniques can be used to interpolate between measured focus points to give a more precise measurement of center of focus. These methods are known in the art, and may be conventionally employed.

As shown in FIG. 2, the field at the center of focus, in this case at −0.1 microns, may not be the same as the field which was arbitrarily taken to be at the zero focus position (0.0) when fields 20 were exposed. For the purposes of focus adjustment, process control, or the like, the zero focus point of the lithography tool may be reset to the value corresponding to the center of focus as determined by the methods of the present invention.

A second preferred embodiment of the present invention does not require the use of a theoretical library or a chosen parameter. In this embodiment, the variation or uniformity of the diffraction signatures obtained from all diffraction structures (or optionally a subset thereof) within a field is determined. The variability may be ascertained by visually comparing these diffraction signatures; however, this method requires operator judgment and is not directly quantifiable, and is also comparatively slow. Accordingly, any of a variety of metrics or methods of analysis may be employed to measuring the variability of these diffraction signatures. Such methods include, but are not limited to, statistical methods such as mean square error (MSE) or root mean square error (RMSE), and other Euclidean distance measures. Such methods also include averaging, weighted averaging, sum of averages and other methods to characterize the difference in diffraction signatures. For example, the larger the RMSE differences between the signatures within a field, the larger the variability, and the further from the center of focus. Alternatively, the overall or peak to peak range of the signature intensities may be used as the measure of variability.

The effect of dose on the center of focus may be analyzed in a similar means. A series of diffracting structures, such as diffracting structures 30, 30', are preferably generated over a determined different focus range encompassing the center of focus, with the dose varied in stepwise fashion from structure to structure. The result is a series of diffracting structures each at a different and known dose. A series of diffraction signatures are then obtained for each diffracting structure, by means of a radiation source-based tool as set forth above. The resulting series of diffraction signatures can be analyzed as above, such as by diffraction signature difference analysis. The resulting center of focus can be plotted against dose, thereby yielding the effect of dose on the center of focus. By this means the dose setting or settings with the most robust focus curves can be ascertained, such that a dose setting with a minimum impact on the focus curve or depth-of-focus can be selected.

Global wafer non-uniformities such as stage tilt, lens aberrations, astigmatism, or the like will increase the variability of diffraction structures distributed across a wafer. However, in the present invention the field that is at the center of focus will still exhibit the minimum variability of diffraction structures within that field when compared with the variability of the diffraction structures in the other fields. Thus the methods of the present invention to find center of focus are still valid despite such global non-uniformities.

These techniques are applicable to metrology tools that have a radiation-based source that can be reflected off of or transmitted through a diffraction structure, and the radiation captured by a detector. In other words, any tool capable of diffraction-based scatterometry measurements can be used in this technique, including but not limited to tools using scatterometry, reflectometry, ellipsometry, or polarimetry. Angular or angle-resolved tools and/or spectral or wavelength-resolved tools may be employed. Additional tools include any tool that can create a response as a function of a tool parameter or combination of tool parameters that result in a diffraction signature. Candidates for diffracting structures suitable for these techniques include but are not limited to photoresist gratings, etched film stack gratings and metal gratings.

This technique can also be used to monitor focus and/or dose and/or layer thickness drifts in a production setting. While monitoring the chosen parameter or variation in diffraction signatures of diffraction structures 30, 30', if the calculated standard deviation exceeds a certain value, the process may be checked for drift. Changes in variation indicate a process shift that should be investigated. In addition, as a general process metrology metric, measuring the structures across an entire wafer and calculating the difference in diffraction signatures can also be used as a model-less approach to wafer uniformity. Low variations in diffraction signatures indicate good process uniformity, while high variations in diffraction signatures indicate poor process uniformity. This applies to many process steps and wafer types, such as the litho, etch, and metals steps in semiconductor manufacturing.

In use of these methods, it may be necessary to utilize various filters and/or related mathematical models to remove outliers that may adversely affect the focus analysis. One such filter is the use of goodness of fit metric of the theoretical diffraction signature to the experimental diffraction signature. Matches with poor goodness of fits may be thrown out of the analysis.

The methods of this invention will find primary application with the photoresist processing step, as determination of best focus is of utmost importance for this step. However, the methods of this invention can also be applied further down the processing line, to determine the "best focus" setting for etched film stacks and metal gratings, or for the "best etch" conditions associated with the etch process.

The methods and devices of this invention may also be used for quality control testing, including analysis of the center of focus determined by other means. This may be done in conjunction with an angle-resolved scatterometer, described above, including its associated computer system, or with other suitable devices capable of making the described measurements.

By means of employing an angle-resolved scatterometer on a periodic structure, the diffraction signature is separated into distinct diffraction orders at angular locations specified by the grating equation:

$$\sin \Theta_i + \sin \Theta_n = n\lambda/d \qquad (3)$$

where $\Theta_i$ is the angle of incidence, taken as negative, $\Theta_n$ is the angular location of the nth diffraction order, $\lambda$ is the wavelength of incident light and d is the spatial period or pitch of the diffraction structure. It can thus be seen that for the $0^{th}$ or specular diffraction order, the angle of incidence is equal to the angular location of the specular diffraction order. However, diffraction orders other than the specular, or general light scatter or diffraction, may be employed, and the appropriate angular location determined as set forth above. Similar relationships govern other modes of generating diffraction signatures, so that with any mode of generating a diffraction signature either the specular diffraction order or some higher diffraction order or general light scatter or diffraction may be employed. For example, in a wavelength resolve device, the angle $\Theta_i$ may be held constant and the wavelength A varied, and the equation solved for $\Theta_n$ at a given n.

The methods and devices of this invention may also be used for determination of the center of focus, whereby the center of focus is adjusted by any suitable means, including use of computer-based control systems, and the methods of this invention used to determine when an acceptable or optimal focus has been determined. The adjustment may be done by dose variations, or by other means known in the art. The invention may be further used for automatic or automated determination and adjustment of the center of focus, utilizing an autofocus control system, wherein at least one input to the autofocus control system includes a parameter relating to the variability of the selected uniformity metric. Thus the present invention may be used for process control of focus.

Thus in one embodiment, the invention provides a diffraction signature measurement device and a controller computer. The controller computer may receive signals from the measurement device, and may determine one or more parameters of a process step, such as focus or dose, as a function of intra-field variability of a plurality of different parameter fields. Determining variability may include direct measures of variability, such as variability in diffraction signatures, as well as variability between a dimension or cross-section of theoretical models of best fit theoretical diffraction signatures. The controller computer may further also receive and optimally output signals to a lithography device, such as controlling a parameter of a process step.

The invention may thus provide for feedforward and feedback control techniques to alter a parameter of a process step. For example, where intra-field variability is outside theoretical or empirically set limits, a parameter of a process step may be altered based on predicted parameters so the process falls within the desired limits. Thereafter, the intra-field variability is determined for one or more fields wherein the parameter of the process step were altered, with comparison to theoretical or empirically set limits. The intra-field variability may be of all, or a subset of, the diffraction structures located in the field or fields of interest.

The diffraction signature measurement device can be employed utilizing a latent image, thereby obviating the need for further wafer processing steps for wafers outside determined acceptable limits. The methods of the invention may further be employed at multiple steps within the wafer processing procedure, such as after exposure, after development, after bake or, in general, after any wafer processing procedure, in order to ascertain the effect of such procedure on "apparent" focus. An increase in intra-field variability in downstream processing procedures indicates that such processing step has had a deleterious effect on CD, such that the variability is indicative of a change similar to a focus change. While such changes are not directly related to the actual focus setting, such change nonetheless provides a metric that may be employed to monitor subsequent processing steps for an increase in intra-field variability related to degradation of the target. Thus the method may further be employed throughout wafer processing.

EXAMPLE 1

Figure 4:
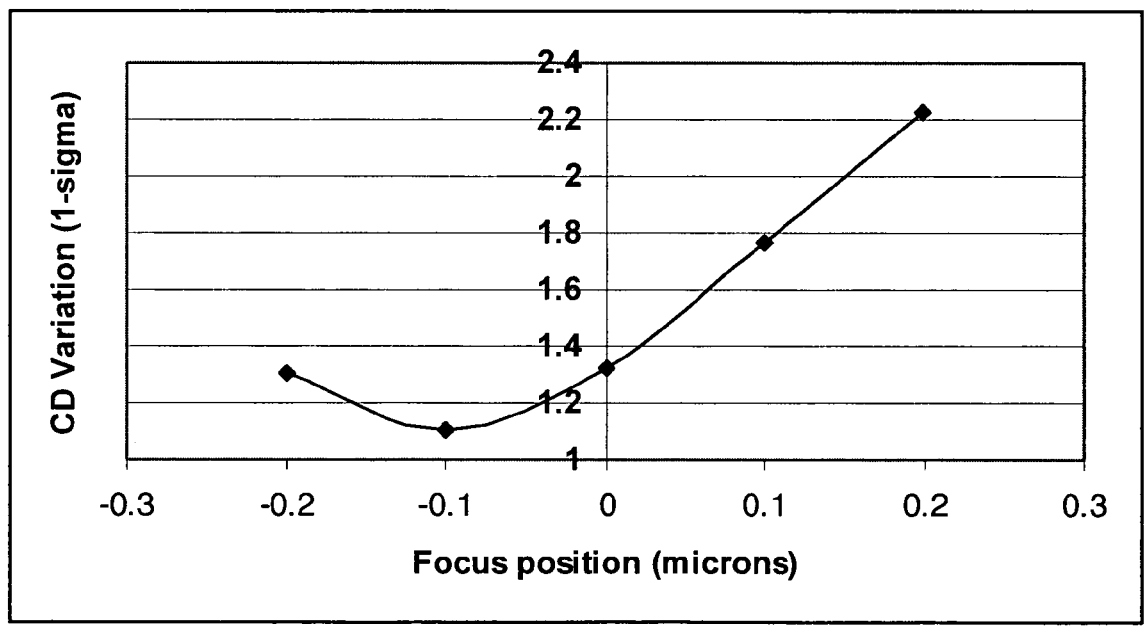
FIG. 4 is a graph of the standard deviation of all measured CDs for each field according to Example 1.

According to the present invention, five fields are exposed at different focus values, taken through focus from −0.2 microns to +0.2 microns in 0.1 micron increments. Each field contains a 5×5 array of equally spaced diffraction structures, similar to that depicted in FIG. 1B. FIGS. 3A–3E graphically display the CDs of the diffraction structures in each field. FIG. 4 is a graph of the 1-sigma standard deviation of the CDs of all 25 diffraction structures in each field. As above, best focus is achieved for the −0.1 micron focus setting.

Figure 5:
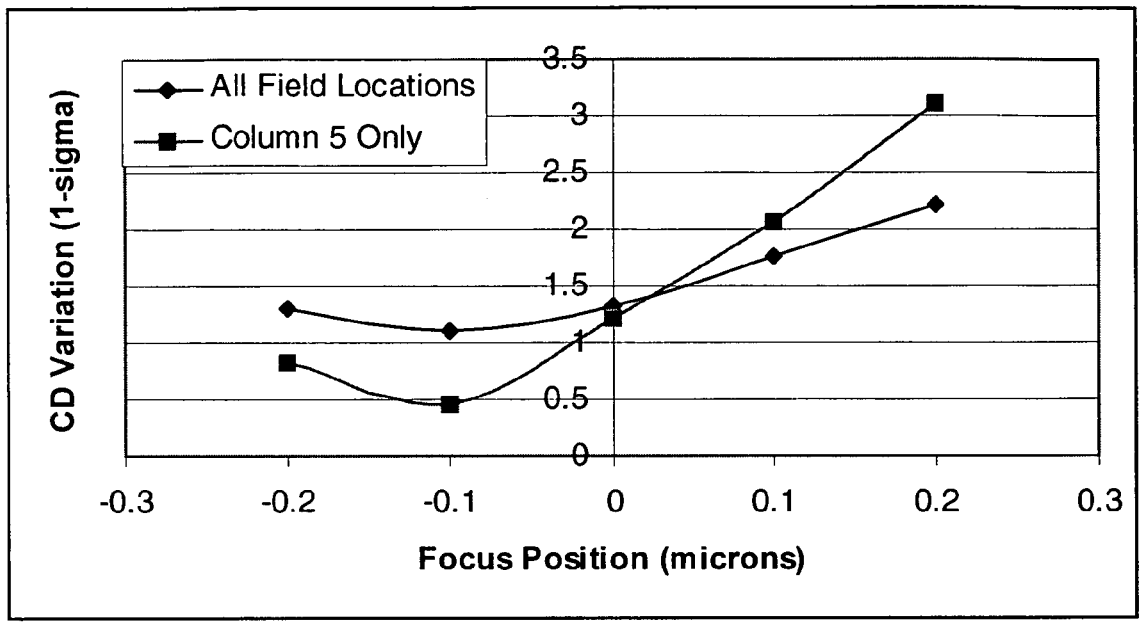
FIG. 5 is the graph of FIG. 4 plus a graph of the standard deviation of a subset of more variable measured CDs for each field according to Example 1.

For real time focus monitoring and process control, it is important to be able to correct for focus drift before it becomes too large. Thus it is advantageous to monitor the CD or other chosen feature of a subset of the diffraction structures which exhibit a larger variation in the chosen feature than the variation of all 25 diffraction structures in each field. For example, chosen features of diffraction structures located in the corners of a field may vary more greatly versus focus than those for structures located in the center of the field. FIG. 5 plots the 1-sigma standard deviation both for all 25 diffraction structures in each field (i.e. the same data as plotted in FIG. 4) and for only the diffraction structures located in column 5 of the 5×5 array in each field. Because the slope is much greater for the subset of five structures than for all 25 structures, the minimum is more easily determined. In addition, by monitoring the chosen feature of only this subset of diffraction structures, focus drift will be detectable more quickly than if all 25 structures were being monitored due to the steeper slope of the curve. This method may also be used to more accurately determine center of focus in the case that the variation vs. focus curve derived from all diffraction structures in each field is close to being flat, with no clear minimum.

Figure 6:
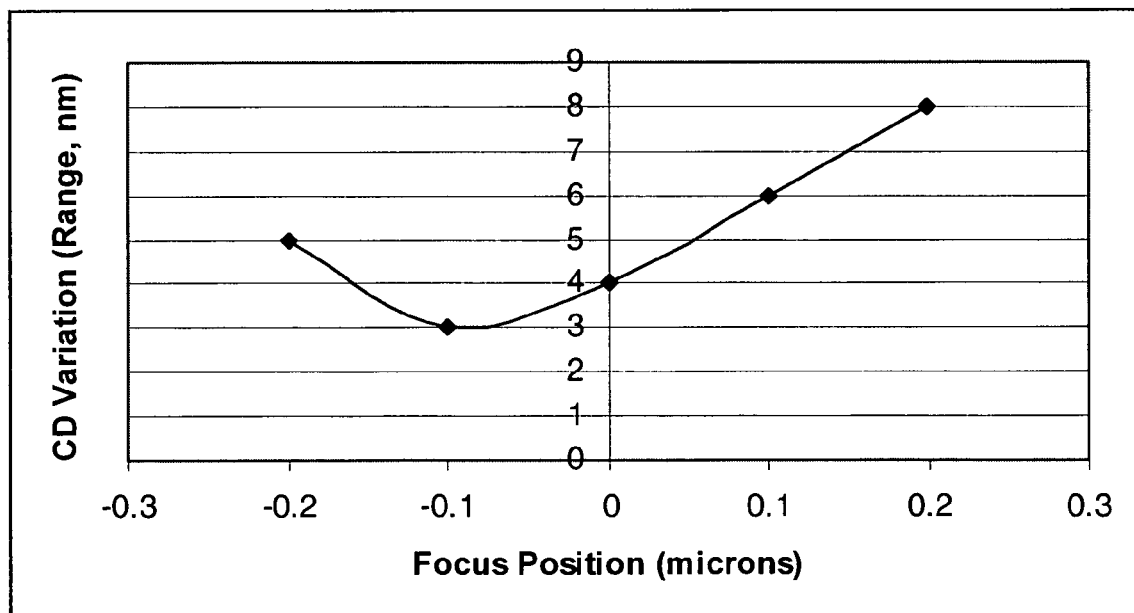
FIG. 6 is a graph of the range of all measured CDs for each field according to Example 1.

FIG. 6 is a graph of the same data as presented in FIG. 4, but instead of graphing the standard deviation of all 25 CDs in each field, the range (maximum minus minimum, in nanometers) of the 25 CD values is plotted. It can be seen that both data sets provide the same result, that the center of focus occurs at the −0.1 micron focus position.

EXAMPLE 2

Figure 7:
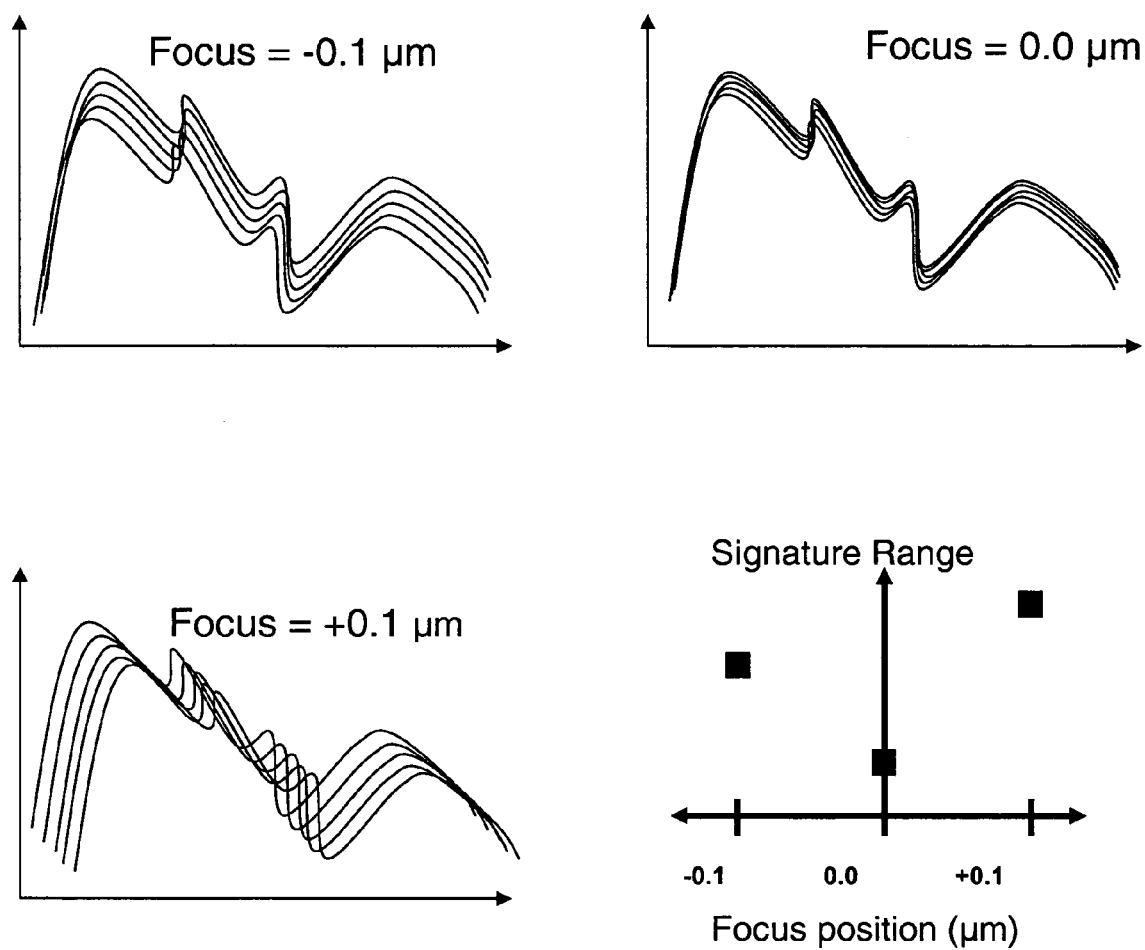
FIG. 7 is a graph illustrating the comparison of diffraction signatures for fields of different focus according to Example 2 of the present invention.

According to the second preferred embodiment discussed above, FIG. 7 depicts the diffraction signatures arising from five spaced diffraction structures within each of three fields shot at different focus values. In this example it is easily determined by inspection that the variation in signatures is minimum for the field shot at the 0.0 micron focus point. The graph in FIG. 7 plots the range, or spread, of the signature intensities for each field. As expected, the minimum value is for the field shot at 0.0 focus, which field is at best focus. This method may be substituted for the embodiment described above for all purposes, including those of process control and focus drift monitoring.

EXAMPLE 3

Figure 8:
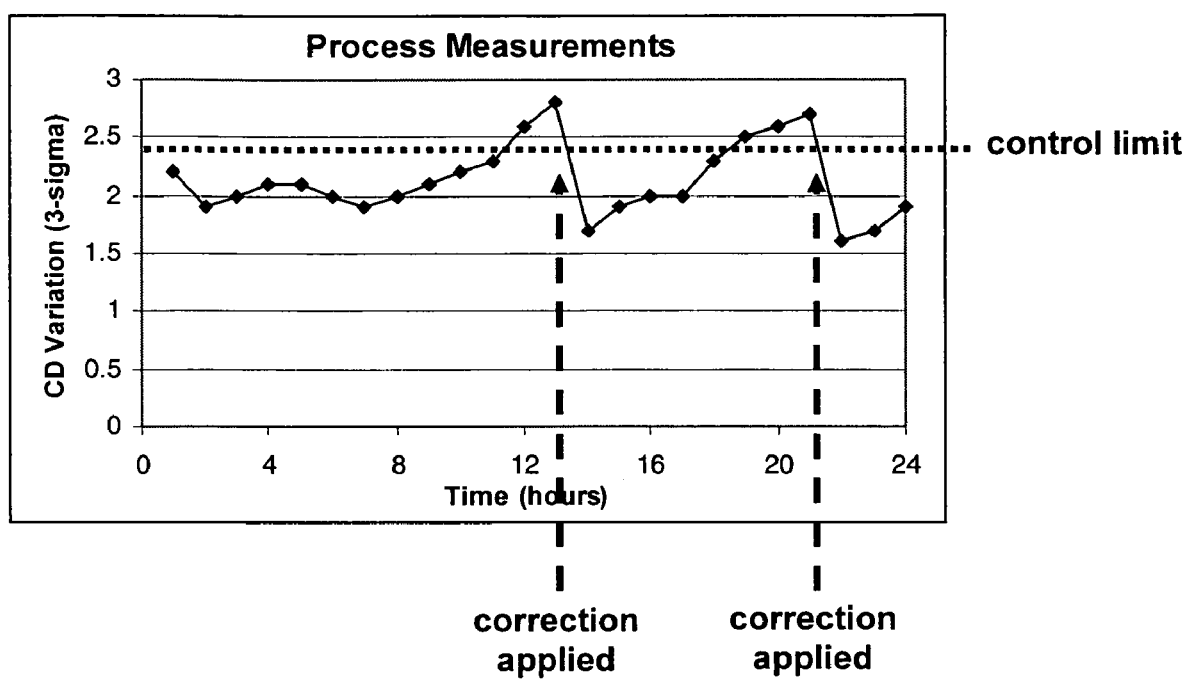
FIG. 8 is a graph illustrating process control measurements according to Example 3 of the present invention.

A typical process control application involves monitoring the variation over time of the chosen feature as multiple wafers printed with the same mask and using the same process are manufactured. FIG. 8 depicts variation of the chosen feature (in this case, variation of CD measured as the 3-sigma of measurements, preferably across the illumination field previously determined according to the methods of the present invention to be at center of focus) measured at one hour intervals. Because the same diffraction structures in the same field are measured for each wafer, and each wafer is printed with the same mask and process, the variability should be the same for each wafer. However, the focus of the lithography tool may drift with time, which leads to higher CD variation, as shown in FIG. 8. Based on prior knowledge an acceptable amount of variation for process control might be 2.4 nm. Hence, a control limit of 2.4 nm is shown in FIG. 8 with a dashed line. Variation within the control limit ordinarily requires little if any scrutiny. If the variation exceeds the control limit and is deemed to be a problem, a focus correction may be applied. In the data of this example, process corrections are applied following the measurement of data at hours 13 and 21. In both cases the CD variation as determined from the next measurements is reduced to well below the control limit.

In this example no process correction was applied when the variation data first exceeded the control limit. This is to avoid over-correcting a problem that might not exist, due to, for example, a purely random fluctuation outside the control limit. The exact rules for control vary from process to process, but the concept of using cross-field variation for controlling focus is the same.

Similar examples can be derived for applications according to the method of present invention for which focus is determined by comparing variation of diffraction signatures taken from all, or a subset of, diffraction structures located across the field. In the case where the variation exceeds some pre-determined signature variation (for example expressed in units of mean square error), a correction would preferably be applied.

The method of this example may be employed for feed-forward and feedback control techniques to alter a parameter of a process step. For example, where intra-field variability is outside theoretical or empirically set limits, a parameter of a process step may be altered based on predicted parameters so the process falls within the desired limits. This process may be automated, and may employ a computer-based control system which collects diffraction signatures, performs a signature variation analysis of diffraction structures in the field, and implements a change in one or more desired parameters of the lithography device, such as for example dose or focus, based on the variation analysis.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method of measuring parameters relating to a lithography device, the method comprising the steps of:
   providing a substrate comprising a plurality of fields, each field having been exposed at a different focus value and comprising a plurality of diffraction structures formed on the substrate by a lithographic process utilizing the lithography device;
   measuring a diffraction signature for each of a plurality of the diffraction structures in a plurality of fields by means of a radiation source-based tool;
   determining for each field the variability of measured diffraction signatures obtained from the plurality of diffraction structures located within that field; and
   comparing the variabilities associated with the fields to determine a desired parameter of the lithography device.

2. The method of claim 1 wherein the substrate comprises a semiconductor wafer.

3. The method of claim 1, wherein measuring a diffraction signature comprises phase measurement by means of a broad spectral radiation source-based tool source, operating at a fixed angle, a variable angle of incidence $\Theta$ or a variable angle of sweep $\phi$.

4. The method of claim 1, wherein measuring a diffraction signature comprises phase measurement by means of a single wavelength radiation source-based tool source, operating at a fixed angle, a variable angle of incidence $\Theta$ or a variable angle of sweep $\phi$.

5. The method of claim 1, wherein measuring a diffraction signature comprises phase measurement by means of a multiple discrete wavelength radiation source-based tool source.

6. The method of claim 1, wherein the diffraction signature is a reflective diffraction signature.

7. The method of claim 1, wherein the diffraction signature is a transmissive diffraction signature.

8. The method of claim 1, wherein the diffraction signature is a specular order diffraction signature.

9. The method of claim 1, wherein the diffraction signature is a higher order diffraction signature.

10. The method of claim 1, wherein the diffraction signature is a measurement of general light scatter or diffraction.

11. The method of claim 1, wherein the desired parameter is dose.

12. The method of claim 1, wherein a value of the desired parameter of the lithography device is determined by a value of the desired parameter associated with the field having a minimum variability of the diffraction signatures.

13. The method of claim 1, wherein the determining step comprises measuring for each field the range of intensities of the diffraction signatures obtained from the plurality of measured diffraction structures located within that field.

14. The method of claim 1, wherein the determining step comprises calculating a statistical measure of the variability.

15. The method of claim 1, wherein the radiation source-based tool comprises a light source-based tool.

16. The method of claim 15, wherein the light source-based tool comprises an incident laser beam source, an optical system focusing the laser beam and scanning through some range of incident angles, and a detector for detecting the resulting diffraction signature over the resulting measurement angles.

17. The method of claim 16, wherein the light source-based tool comprises an angle-resolved scatterometer.

18. The method of claim 15, wherein the light source-based tool comprises a plurality of laser beam sources.

19. The method of claim 15, wherein the light source-based tool comprises an incident broad spectral light source, an optical system focusing the light and illuminating through some range of incident wavelengths, and a detector for detecting the resulting diffraction signature over the resulting measurement wavelengths.

20. The method of claim 15, wherein the light source-based tool comprises an incident light source, components for varying the amplitude and phase of the S and P polarizations, an optical system focusing the light and illuminating over some range of incident phases, and a detector for detecting the phase of the resulting diffraction signature.

21. The method of claim 1, the method further comprising forming the plurality of diffraction structures at known different focus settings and known different dose settings and determining the effect of dose on focus.

22. The method of claim 21, wherein the plurality of diffraction structures comprise sets of the same known different focus setting diffraction structures, the sets varying by different known dose settings.

23. The method of claim 1, wherein the desired parameter is center of focus.

24. A method of process control for center of focus in a lithography device, the method comprising the steps of:
   determining the center of focus of the lithography device according to the method of claim 23; and
   adjusting the focus setting of the lithography device to the determined center of focus.

25. The method of claim 24, wherein the adjusting step comprises utilizing a computer-based control system.

26. The method of claim 24, wherein the adjusting step comprises an autofocus control system, wherein at least one input to the autofocus control system comprises a measure relating to a minimum variability.

27. The method of claim 1, wherein the determining step comprises
   providing a library of theoretical diffraction signatures generated from theoretical diffraction structures;
   determining in the library a best match theoretical diffraction signature for each measured diffraction signature;
   associating a chosen feature of the best match theoretical diffraction signature with the measured diffraction signature; and
   determining for each field the variability of the chosen feature associated with the plurality of diffraction structures located within that field.

28. The method of claim 27, wherein the chosen feature is critical dimension (CD).

29. The method of claim 27, wherein the chosen feature is a cross-section area.

30. The method of claim 27, wherein the chosen feature is a cross-section volume.

31. The method of claim 27, wherein the chosen feature is a product of two or more features of the theoretical diffraction structure providing the matching theoretical diffraction signature.

32. The method of claim 27, wherein the determining step comprises measuring for each field the range of the chosen features associated with the plurality of measured diffraction structures located within that field.

33. The method of claim 27, wherein the determining step comprises calculating a statistical measure of the variability.

34. The method of claim 33, wherein the statistical measure is a standard deviation of the chosen features.

* * * * *